(12) United States Patent
Peters et al.

(10) Patent No.: US 7,611,072 B2
(45) Date of Patent: Nov. 3, 2009

(54) METHOD AND DEVICE FOR ATOMIZING LIQUID

(75) Inventors: Ralf-Peter Peters, Bergisch-Gladbach (DE); Holger Holakovsky, Witten (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 557 days.

(21) Appl. No.: 11/427,412

(22) Filed: Jun. 29, 2006

(65) Prior Publication Data

US 2008/0048054 A1 Feb. 28, 2008

(30) Foreign Application Priority Data

Jun. 29, 2005 (DE) ............. 10 2005 030 803
Jun. 29, 2005 (DE) ............. 20 2005 010 349 U (51) Int. Cl.
*B01F 3/04* (2006.01)
(52) U.S. Cl. ............. 239/13; 239/136; 261/78.2; 261/142; 261/DIG. 65; 392/394
(58) Field of Classification Search ............. 261/78.2, 261/142, DIG. 65; 122/28; 239/13, 136, 239/523, 524; 392/394, 399
See application file for complete search history.

(56) References Cited

U.S. PATENT DOCUMENTS

| | | | |
|---|---|---|---|
| 1,574,856 A * | 3/1926 | Armbruster, Jr. et al. ..... 126/113 |
| 1,683,760 A * | 9/1928 | Conners ............. 40/407 |
| 1,846,478 A * | 2/1932 | Earman ............. 261/115 |
| 2,437,963 A * | 3/1948 | Langmuir et al. ............. 516/8 |
| 2,755,135 A * | 7/1956 | Gusching ............. 239/524 |
| 3,084,874 A * | 4/1963 | Jones et al. ............. 239/8 |
| 3,747,851 A | 7/1973 | Conrad |
| 3,850,373 A | 11/1974 | Grolitsch |
| 3,873,029 A | 3/1975 | Mihaly |
| 3,918,645 A | 11/1975 | Mohler |
| 3,923,248 A | 12/1975 | Cresswell |
| 4,055,305 A | 10/1977 | Schwinn |
| 4,067,798 A | 1/1978 | Hauschildt et al. |
| 4,194,693 A | 3/1980 | Mikulesky |
| 4,349,157 A | 9/1982 | Beiswenger et al. |
| 4,349,723 A * | 9/1982 | Swiatosz ............. 392/399 |
| 4,356,974 A | 11/1982 | Rosenberg et al. |
| 4,391,410 A | 7/1983 | Smith |
| 4,531,677 A * | 7/1985 | Suzuki et al. ............. 239/520 |
| 4,585,069 A | 4/1986 | Whitaker |
| 4,625,915 A | 12/1986 | Cockman |
| 4,660,765 A | 4/1987 | Rosenberg |
| 4,711,399 A | 12/1987 | Rosenberg |
| 4,813,610 A | 3/1989 | Renowden |
| 4,815,665 A | 3/1989 | Haruch |

(Continued)

FOREIGN PATENT DOCUMENTS

DE 1698735 4/1955

(Continued)

*Primary Examiner*—Scott Bushey
(74) *Attorney, Agent, or Firm*—David S. Safran; Roberts Mlotkowski Safran & Cole, P.C.

(57) ABSTRACT

A method and a device for the atomization of a liquid by directing a jet of liquid onto a hot contact surface, in particular a deflecting surface, so that a part of the liquid is vaporized. The non-vaporized liquid is atomized into small droplets that form an aerosol.

24 Claims, 6 Drawing Sheets

U.S. PATENT DOCUMENTS

| | | |
|---|---|---|
| 4,828,182 A | 5/1989 | Haruch |
| 4,886,112 A | 12/1989 | Vinson |
| 4,945,929 A | 8/1990 | Egilmex |
| 5,017,343 A | 5/1991 | Cetinkaya |
| 5,114,076 A * | 5/1992 | Imai et al. .................. 239/338 |
| 5,137,214 A * | 8/1992 | Mallery ....................... 239/11 |
| 5,241,954 A | 9/1993 | Glenn |
| 5,261,949 A | 11/1993 | Schilling |
| 5,461,695 A | 10/1995 | Knoch |
| 5,839,667 A | 11/1998 | Fishcer |
| 5,964,223 A | 10/1999 | Baran |
| 6,196,218 B1 | 3/2001 | Voges |
| 6,336,599 B1 | 1/2002 | Herr et al. |
| 6,443,146 B1 | 9/2002 | Voges |
| 6,503,362 B1 | 1/2003 | Bartels et al. |
| 6,622,938 B2 * | 9/2003 | Fischer et al. ............... 239/124 |
| 6,705,548 B2 | 3/2004 | Bendig et al. |
| 7,143,766 B2 * | 12/2006 | Schuster et al. ........ 128/203.26 |
| 2002/0020764 A1 | 2/2002 | Bendig et al. |
| 2002/0020767 A1 | 2/2002 | Pyo |
| 2002/0023975 A1 | 2/2002 | Bendig et al. |
| 2003/0102337 A1 | 6/2003 | Walter |
| 2003/0102392 A1 | 6/2003 | Walter |
| 2003/0146303 A1 | 8/2003 | Johnson |
| 2004/0046040 A1 | 3/2004 | Micheli |
| 2004/0140375 A1 | 7/2004 | Hakala |
| 2004/0227016 A1 | 11/2004 | Yagi et al. |
| 2005/0001066 A1 | 1/2005 | Miyamoto et al. |
| 2005/0042170 A1 | 2/2005 | Jiang et al. |

FOREIGN PATENT DOCUMENTS

| | | |
|---|---|---|
| DE | 2218709 | 10/1973 |
| DE | 2209346 C3 | 4/1980 |
| DE | 3103902 A1 | 12/1982 |
| DE | 3612473 C2 | 10/1987 |
| DE | 29612115 U1 | 9/1996 |
| DE | 19925777 A1 | 1/2000 |
| DE | 19854005 C2 | 5/2000 |
| EP | 0471323 A1 | 2/1992 |
| EP | 0653218 A1 | 5/1995 |
| EP | 1023911 A2 | 8/2000 |
| FR | 2682049 A1 | 4/1993 |
| GB | 744547 A | 2/1956 |
| GB | 2120958 A * | 12/1983 |
| GB | 2214088 A | 8/1989 |
| WO | 9114468 A1 | 10/1991 |
| WO | 9204065 A1 | 3/1992 |
| WO | 9219383 A1 | 11/1992 |
| WO | 9518681 A1 | 7/1995 |
| WO | 9712687 A1 | 4/1997 |
| WO | 9807464 A1 | 2/1998 |
| WO | 03047763 A1 | 6/2003 |
| WO | 2004050258 A1 | 6/2004 |
| WO | 2005005056 A1 | 1/2005 |
| WO | 2005080001 A1 | 9/2005 |

* cited by examiner

METHOD AND DEVICE FOR ATOMIZING LIQUID

BACKGROUND OF THE INVENTION

1. Field of the Invention

The present invention relates to a method and a device for atomizing (nebulising) a liquid, in particular a liquid medicament formulation, as well as a method for the production of such a device.

2. Description of Related Art

In the atomization of a liquid medicament formulation, the object is to convert, as much as possible, an accurately-defined amount of active constituent into an aerosol for inhalation. The aerosol should be characterized by a small mean value of the droplet size with a narrow droplet size distribution and by a small momentum (low propagation rate).

The expression "medicament formulation" used in the present invention is understood to include, apart from medicaments, also therapeutic agents or the like, in particular therefore all types of agents for inhalation. The present invention is however not restricted to the atomization of agents for inhalation, but in particular may also be employed for cosmetic agents or other liquids and possibly also for suspensions or the like, even if the following description is primarily directed to the preferred atomization of a medicament formulation for inhalation.

The term "aerosol" is understood in the context of the present invention to mean a preferably nebulous collection of a large number of droplets of the atomized liquid with preferably a substantially non-directed (random) and/or broad spatial distribution of the directions of movement and preferably with low velocities of the droplets.

International Patent Application Publications WO 92/04065 A1 (U.S. Pat. No. 5,178,138) and WO 03/047763 A1, European Patent Applications EP 0 471 323 A1 and EP 0 653 218 A1 and U.S. Pat. No. 5,241,954 disclose nebulisers for liquids for inhalation purposes. The liquid is, in each case, mixed with a gas stream and directed onto a deflecting surface to effect nebulisation. This is complicated and is not always effective, and in particular the droplet size may vary greatly.

International Patent Application Publication WO 92/19383 A1 discloses an atomization of a liquid without an additional gas stream or compressed air. A liquid jet is directed onto a conical deflecting surface for the atomization, so that the liquid is atomized in a plane transverse to the axis of the cone, in order to generate droplets with a diameter of less than 10 µm for inhalation purposes. It is difficult to generate an aerosol in this way having a defined droplet size and a narrow, constant droplet size distribution.

U.S. Pat. No. 5,261,949 relates to a method of producing an atomized liquid to be conveyed in a stream of a carrier gas and to an apparatus for implementing the method. A liquid mist for being conveyed by a carrier gas stream is produced from a liquid by atomizing the liquid into the carrier gas stream in the form a collection of droplets, deflecting the collection of droplets in the carrier gas stream at a deflection region, separating droplets in the collection of droplets which exceed a maximum size from the carrier gas stream, collecting at least a part of the separated droplets on at least one heatable contact surface, and at least partially vaporizing them into the carrier gas stream. This method requires a first aerosolization of the liquid in a spray of droplets and a second aerosolization of the larger droplets by means of the heatable contact surface. A further disadvantage is that a carrier gas stream is necessary. This makes it difficult or even impossible to generate an aerosol with the desired characteristics, in particular a low propagation rate. Moreover, the method is not suitable for inhalers to generate a defined aerosol of a medical formulation.

French Patent FR 2 682 049 A1 relates to a device for generating a mixture of air and vapor of hydrogen peroxide. The device comprises a nozzle for atomizing the liquid hydrogen peroxide pneumatically and generating a mixture of air and droplets of hydrogen peroxide. This aerosol is directed onto a contact surface heated to about 200° C. Thus, the droplets of hydrogen peroxide shall be vaporized so that vapor of hydrogen peroxide is generated.

UK Patent Application GB 2 214 088 A relates to a heated nebulizer system for producing a humidified and heated breathing gas to be inhaled by a patient undergoing inhalation therapy. Pressurized oxygen is discharged via a nozzle and generates an aerosol spray of liquid water and ambient air. This aerosol is directed in a conical pattern onto an annular heated surface upon which the aerosol impinges. The heated surface volatilizes at least a portion of the aerosol while allowing the remainder to coalesce and return through a port to a reservoir of the liquid water, Thus, it is desired to generated water vapor so that humidified and heated gas can be breathed.

UK Patent Application GB 744,547 A relates to a method for thermal production of an aerosol of an insecticide, such as DDT, bactericide or the like active material in which a solution or dispersion of the active material in a more volatile vehicle is caused to impinge onto a surface, heated to a temperature above the boiling point of the vehicle. As the result of the consequent rapid boiling of the vehicle, the latter assumes a state in which the bulk phase of the boiling material is separated from the hot surface by a layer of vapor of the vehicle. The liquid is discharged either between two heated plates or though a conduit surrounded by the heating jacket. This method is not suitable for generating a defined aerosol with the desired characteristics, in particular with low propagation rate and/or small particle size.

The Canon company markets under the model number "i850" a printer operating according to the so-called bubble jet principle. The printer comprises a plurality of nozzle openings with a diameter of 10 µm for ejecting ink droplets with a volume of 2 pl, i.e., with a diameter of about 12 µm. Liquid chambers in which the ink is vaporized by means of an electrothermal element are associated with the nozzle openings. The change in volume occurring on vaporization leads to the ejection of the ink droplets through the nozzle openings. In order to achieve the desired resolution of for example 4,800 dpi, the ink droplets are ejected at high velocity (10 m/sec or more) in a specific direction through a nozzle.

In the bubble jet principle, a complicating factor is that the ejection of the individual droplets and accordingly the renewed vaporization of ink have to be controlled individually for the individual nozzles, in order to achieve a desired print image. Apart from the timing, the site and momentum of the formed droplet are important in the bubble jet principle. For this reason, the print head comprises a plurality of individual heaters, ink chambers and nozzles, in which each configuration of heater, ink chamber and nozzle can generate and eject individual droplets only in succession. Such a print head is complicated and expensive to manufacture. A very large number of nozzles is required to achieve the droplet rate that is normally necessary for an inhaler. In addition there is the danger of the undetected stoppage or blockage of individual nozzles as well as the failure of individual heating elements, for example due to deposits or the like. Moreover, when the bubble jet principle is employed for medicament formulations further undesirable effects, such as a build-up of active constituent, reactions of the active constituent, or the like, may occur.

SUMMARY OF THE INVENTION

A primary object of the present invention is to provide a method and a device for atomizing a liquid as well as a method for the production of such a device, so as to enable an effective atomization of the liquid and the generation of an aerosol in a simple and effective way, in particular where the aerosol has a small droplet size of on average preferably less than 10 μm diameter, a narrow and constant droplet size distribution and/or a low propagation rate, and/or so as to enable a simple and inexpensive production.

The above object is achieved by the present invention by vaporizing a small proportion of the liquid in order to atomize the remaining liquid into small droplets, more specifically, in contrast to the aforementioned bubble jet principle, in a non-directed manner, i.e., at least with a very broad spatial velocity distribution of the droplets, in order thereby to generate an aerosol. This enables an aerosol having the desired properties to be generated in a very simple and effective manner.

According to the present invention, the liquid is directed in the form of a, preferably, free jet onto a hot contact surface, in particular, a warmed or heated deflecting surface. When the jet strikes the surface a small proportion of the liquid undergoes a spontaneous transition from the liquid to the gaseous phase. On account of the spontaneous vaporization of the liquid occurring above a certain temperature, a very high pressure is produced that ejects or dissolves out, as droplets, a specific amount of liquid from the jet. On the one hand, only a small part of the incident liquid is thereby vaporized. On the other hand, the residence time of the unvaporized liquid is very short, which means that the unvaporized liquid is scarcely heated. This last fact is of great advantage, in particular in the case of heat-sensitive medicament formulations. In contrast to conventional deflecting surfaces, the incident velocity is not, or is only slightly, relevant for the atomization; instead, the energy for the atomization is primarily provided by the vapor pressure of the vaporized liquid and accordingly the atomization is determined at least substantially by the temperature of the contact element. The velocity of the incident liquid, in particular the jet, on the other hand, primarily determines the aerosol stream and the droplet rate.

In the present invention, the term "jet" preferably means that the liquid is discharged or ejected in a continuous manner, in particular, like a column of liquid. Therefore, such a jet is preferably neither a spray of droplets nor an aerosol, although the jet (column of liquid) may be interrupted and may be composed of multiple segments of liquid or the like.

Most preferably, any aerosolization of the liquid is not necessary and not provided before the partial vaporization on the contact surface. Instead, the liquid is directed only in the form of a preferably focused or defined jet onto the hot or heated contact surface. Thus, a very simple, inexpensive and/or compact construction is possible.

In particular, in contrast to the previously known mechanical atomization methods, in the solution according to the present proposal, substantially lower pressures are sufficient to deliver the liquid. The atomization per se takes place in fact preferably at least substantially due to the vaporization and, most preferably, only by the vaporization. The phase transition from the liquid to gaseous state leads in fact to a sharp increase in volume, in the case of water by a factor of ca. 1700. This sudden change in volume leads to a marked increase in kinetic energy and permits a spontaneous splitting of the liquid into individual, very small droplets.

In addition, it is sufficient to vaporize only a small proportion of the liquid in order to achieve the desired atomization effect. Thus, an aerosol having the desired properties, in particular, a small droplet size, narrow and constant droplet size distribution and/or low propagation rate, can be generated very simply and effectively.

In particular, the atomized liquid droplets together with the ambient atmosphere form the aerosol. The liquid is accordingly preferably gas-free, i.e., is formed only of a liquid phase and in particular contains no dissolved propellant gas or the like.

Preferably, small amounts of the liquid are atomized in succession. This permits an at least substantially uniform distribution of the energy in the respective amount of liquid to be atomized, and thereby produces a very uniform, narrow size distribution of the liquid droplets formed in the atomization.

The successive atomization and discharge of small amounts of the liquid, in particular doses of a medicament formulation, e.g., of 10 to 100 μl, may take place continuously or discontinuously. Preferably, a continuous jet with a small diameter is generated from the liquid, which is then atomized by partial evaporation of the liquid to generate the desired aerosol. However, the jet may also be interrupted.

Alternatively or in addition, the aforementioned small amounts of liquid may also be atomized in parallel, i.e., over parallel flow paths, jets and/or at separate locational regions, and in particular, simultaneously.

Particularly preferably, the liquid is atomized into droplets without using side walls. This is compatible Faith the formation of a nebulous aerosol having a preferably low propagation rate, in particular a quasi-stationary aerosol cloud.

The phase transition and vaporization takes place on contact with the contact or deflecting surface, preferably without any delay in boiling. The temperature of the contact element and the contact surface, for this purpose, preferably, is significantly greater than the vaporization temperature of the liquid or of a constituent of the liquid, such as a solvent or the like. This leads to the spontaneous vaporization and to the desired atomization of the non-vaporized liquid. The produced liquid droplets then form the desired aerosol.

In particular, when the liquid strikes the contact or deflecting surface there is a sudden, discontinuous formation of a vapor cushion between the hot surface and the actual jet. This leads to the successive atomization, already mentioned above, of small amounts of the liquid and accordingly to substantially uniformly large liquid droplets.

The liquid jet may be employed as required for an unmetered or a metered atomization and aerosol generation. The metering by means of the jet is used especially for the atomization of medicament formulations, in particular for inhalation purposes. The solution according to the present proposal leads to an atomization of a very defined proportion of the delivered liquid, so that the metering of the jet leads to an accurate metering of the atomized liquid and thus of the ejected medicament and active constituent.

The atomization according to the present proposal, in addition, also leads to extremely reproducible properties, such as a narrow and constant droplet size distribution, uniform mean droplet diameter and/or narrow droplet velocity distribution, with in particular a low mean velocity of the aerosol. This is very advantageous when metering medicaments, active constituents or the like, since, for example, a defined proportion of droplets that reaches the lungs and that can be effectively absorbed can always be generated.

Further aspects, features, properties and advantages of the present invention are disclosed in the following detailed description of preferred embodiments with reference to the accompanying drawings.

DETAILED DESCRIPTION OF THE INVENTION

In the figures, the same reference numerals are used for identical or similar parts, even when the description is not repeated.

Figure 1:
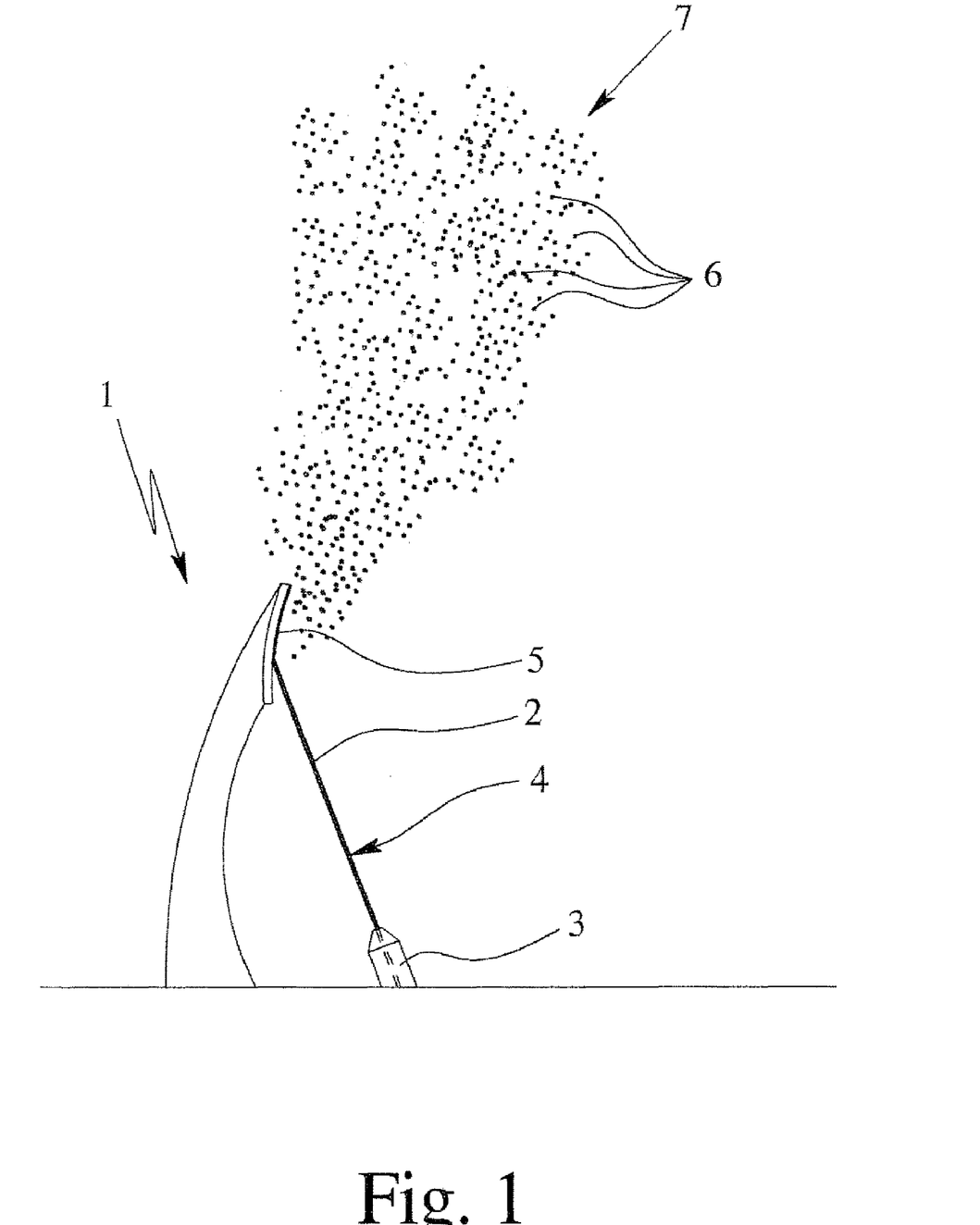
FIG. 1 is a diagrammatic view of a device in accordance with a first embodiment of the invention.

The schematic diagram according to FIG. 1 diagrammatically shows a device 1 in accordance with a first embodiment of the invention. The device 1 serves for the atomization of a liquid 2, in particular, a liquid medicament formulation in the sense mentioned in the introduction, a cosmetic agent, an industrial liquid, or the like.

The device 1, preferably, comprises a nozzle 3 for generating a jet 4 of the liquid 2. In particular a free, i.e., non-laterally-directed jet 4, is formed. The jet 4, preferably, has an at least substantially circular cross-section with a diameter of, in particular, 1 to 50 μm, especially, less than 20 μm or even less than 10 μm. The jet 4 is ejected from the nozzle 3, preferably, at a pressure of 0.05 to 3 MPa, in particular, 0.1 to 0.3 MPa.

Furthermore, the device 1 comprises a hot or heatable contact surface 5 on which the jet 4 is incident.

The contact surface 5 may, in principle, have any suitable shape that is appropriate for the desired atomization, and thus, for example, may be formed in a grid like manner or provided with openings. Preferably, the contact surface 5 forms an, in particular, a continuous impact and deflecting surface for the jet 4.

The contact surface 5 can be warmed or heated by means of a heating device (not illustrated in FIG. 1), in order to partially vaporize the incident liquid 2 and thereby achieve the desired atomization of the liquid 2. Preferably, only up to 15 Vol. %, in particular, more than 1 or 2 Vol. % and/or less than 10 Vol. %, most preferably, about 7 Vol. % or less, of the supplied liquid 2 is vaporized. The heating device preferably operates electrically. However, heating or input of thermal energy may also take place in any other convenient way, in particular by light or chemical processes, such as oxidation of a fuel by means of a catalyst.

The temperature of the contact surface 5 is, preferably, significantly above (e.g., by 20° C. or 50° C.) the boiling point of the liquid 2 or of an essential constituent of the liquid 2, such as a solvent. When water is used as solvent, the temperature of the contact surface 5 is, preferably, at least 120° C., in particular, 150° C. or more. Preferably, the starting temperature (temperature at the beginning just before the liquid 2 impinges on the contact surface 5) is kept at about 250° C. or more, in particular, up to 400° C. Thus, a spontaneous vaporization without a delay in boiling can be achieved, i.e., a direct transition from the liquid to the gaseous state together with the desired increase in volume.

The temperature of the contact surface 5 is also, preferably, so high that no residues or at least no residues relevant for a medical application are formed on the contact surface 5, in particular as regards the optimized composition or formulation of the liquid 2 for such an application.

Another aspect is the dispensing ratio or liquid flow (volume of liquid before partial vaporization per time unit). Preferably, the liquid flow is 5 to 100 μl/s, in particular, about 10 to 50 μl/s.

The contact surface 5 is preferably formed of metal, semiconductor material such as silicon, ceramics or glass. In particular the contact surface 5 is formed by the surface of a corresponding plate-shaped piece, side wall or a corresponding coating. Alternatively or in addition, the material and/or the contact surface 5 may be coated, for example, with one of the aforementioned materials or with silicon nitride, silicon carbide, polytetrafluoroethylene (PTFE) or other suitable materials, in particular, to minimize or prevent formation of residues and/or dirt.

The thermal capacity of the body forming the contact surface 5 is, preferably, sufficiently large to maintain the surface temperature sufficiently constant during the atomization process. The thermal capacity is however preferably chosen to be not too large, so that the heat loss of the heating device (not shown) associated with the contact surface 5 can be minimized or at least kept to acceptable limits. Alternatively or in addition, the heating device (heater) responds sufficiently rapidly so that the temperature can be maintained at least in a desired range during the atomization process.

In particular, the following equation is at least essentially fulfilled:

$$(0.001 \cdot T^{1.9}/(1+0.32 \cdot dV/dt) - 4.7 \cdot e^{-0.053(dV/dt+5)}) \cdot V = 1000 \cdot (m_H \cdot c_H \cdot \Delta T + E_{zu})/(c_F \cdot (100 - T_R) + q_F + 0.4 \cdot (T - 100 - \Delta T/2))$$

with:

T temperature of heater at the beginning of dispensing, in ° C.;

V total volume of dispensed liquid per dose, in μl;

dV/dt liquid flow, in μl/s;

$m_H$ mass of heater, in g;

$c_H$ specific heat capacity of heater, in J/(g·K);

ΔT amount of temperature change of the heater during
  1. dispensing action, in K;

$E_{zu}$ additional energy supply to the heater during dispensing
  2. action, in K;

$c_F$ specific heat capacity of liquid, in J/(g·K);

$T_R$ room or environment temperature $q_F$ specific heat of evaporation of liquid, in J/g.

Preferably, the total volume of liquid dispensed per dose or actuation of the dispensing device 1 is about 10 to 100 μl in particular about 15 to 60 μl.

Particularly preferably, the pressure with which the jet 4 impacts on the contact surface 5 can be adjusted, controlled or regulated. In particular, this is achieved by adjusting, controlling or regulating the pressure at which the jet 4 exits from the nozzle 3. Alternatively or in addition, the distance between the nozzle 3 and contact surface 5 and/or the impact point on the contact surface 5 can, to this end, also be varied, for example, by altering the direction of the jet or using another nozzle 3.

The distance of the nozzle 3 from the contact surface 5—i.e., the free jet length—preferably, is small, and in particular, is less than 1 mm. Preferably, the distance is less than 500 μm, and in particular, is basically 100 to 300 μm. Thus, a relatively low feed pressure and/or exit pressure at the nozzle 3 is sufficient to allow the liquid 2 to strike the contact surface 5 still with a relatively high or at least sufficient pressure of preferably 0.05 to 3 MPa, in particular 0.1 to 0.3 MPa.

When the liquid 2 or the jet 4 strikes the contact surface 5, only a very small proportion of the liquid 2 is spontaneously vaporized. In particular, a vapor cushion is intermittently formed between the contact surface 5 and the actual jet 4 and the non-vaporized liquid 2. The increase in volume during the transition from the liquid to the gaseous phase leads to the desired atomization of liquid 2 into very small, substantially uniformly large droplets 6 that form an aerosol 7 together with the ambient atmosphere, in particular air.

The contact surface 5 is, preferably, formed substantially microscopically smooth, at least in its impact region. The contact surface 5 may if necessary be structured macroscopically and/or microscopically—i.e., provided with protuberances and/or depressions—or formed smooth, in order to influence the aerosol formation in a desired way. In particular, a microstructuring of the contact surface 5 can improve the efficiency of the atomization, in that the vaporization of liquid 2 takes place in open microcavities. Due to the microcavities the vaporized liquid and the energy thereby ejected can be focused on or directed at the following liquid 2 in the jet. Alternatively or in addition, the contact surface 5 may also be formed micro-rough. Different reflection properties are thereby produced. This is conducive to a broad spatial distribution and angular distribution of the velocities of the resultant droplets 6, and thus produces a "diffuse scattering".

Preferably, the droplets 6 have a narrow and uniform size distribution. In particular, a constant impact velocity of the liquid 2 on the contact surface 5 is conducive to a uniform size distribution, since each liquid element is thereby subjected to uniform dynamical and thermal influences, which is conducive to the desired uniformity of the droplet size.

However, in order to assist a specific spatial localization of the droplets 6 and the formation of a defined aerosol cloud, the contact and deflecting surface 5, preferably, has a concave, for example, parabolic, shape. In addition or alternatively, guidance devices (not shown) for the aerosol 7 or means to produce swirling or deflection of the aerosol 7 or the like may be provided.

The droplets 6 formed in the atomization, preferably, have no substantially uniform velocity direction, but in particular exhibit a broad spatial distribution of the directions and angular distribution of their velocities. This broad spatial velocity distribution is assisted by the preferred deflection and the preferred reflection of the liquid 2 at the contact and deflecting surface 5.

In addition, the deflection and/or the reflection of the liquid 2 at the contact and deflecting surface 5, as well as preferably the diffused spatial distribution of the movement directions of the droplets 6, are conducive to the formation of a quasi-stationary aerosol cloud or at least to a substantial decrease in the propagation velocity of the aerosol 7 and the velocities of the droplets 6, in particular, to less than 1 m/sec immediately after the contact surface 5.

The impact angle of the jet 4 on the contact surface 5, i.e., the angle between the jet 4 and the contact surface 5, is preferably between 10° and 90°, in particular, between 40° and 70°.

The droplets 6 preferably have a mean diameter of less than 10 μm, in particular, of 1 to 7 μm, most particularly preferably, of substantially 5 μm or less, in order to achieve a high pulmonary accessibility during inhalation.

The mean volume of the droplets 6 is preferably less than 1 pl, in particular, substantially 0.1 pl or less.

The volume flow of atomized liquid 2 is preferably at least 30 μl/sec. Thus, the amount of aerosol 7 appropriate for an inhalation can be generated with a sufficient amount of an active constituent in a sufficiently short time of, for example, only one second or a few seconds.

A metering of the jet 4 preferably takes place. Thus, the aerosol 7 and thereby the ejected amount of medicament formulation or the like can be metered in a simple and effective manner.

The generation of the aerosol 7 is preferably followed by inhalation by a user (not shown). The device 1 is accordingly preferably designed as an inhaler or for medical aerosol treatment.

However, the aerosol 7—in particular depending on the liquid 2 that is used—may also be employed for other purposes, in particular, for cosmetic or technical purposes. This has already been discussed in the introduction.

Further embodiments according to the present invention are described hereinafter with the aid of the further figures, the respective description concentrating on essential differences compared to the other embodiments. Descriptions and explanations regarding the other embodiments and in the introductory part thus apply as appropriate or suitably amplified.

Figure 2:
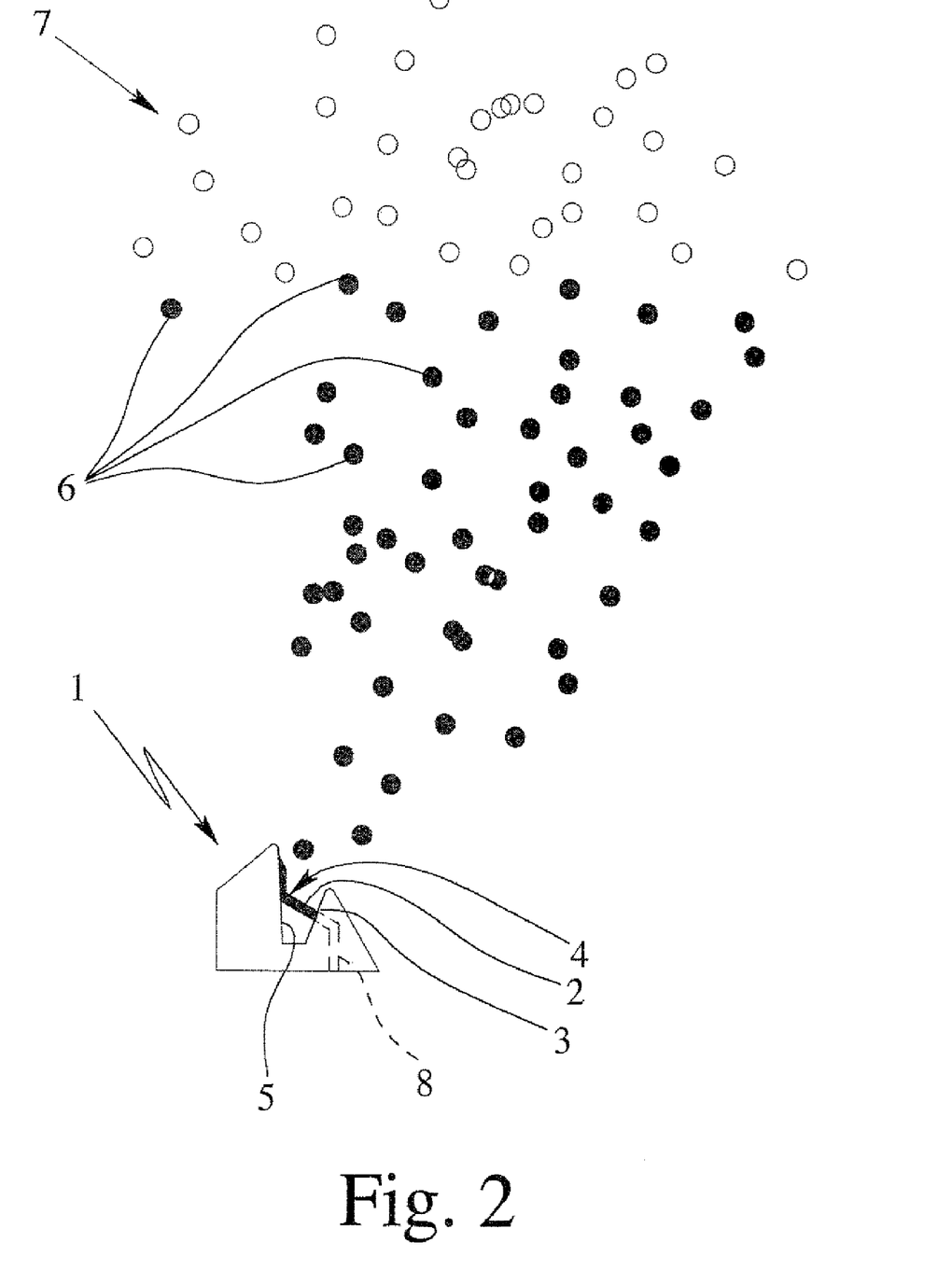
FIG. 2 is a diagrammatic view of a device in accordance with a second embodiment of the invention.
Figure 3:
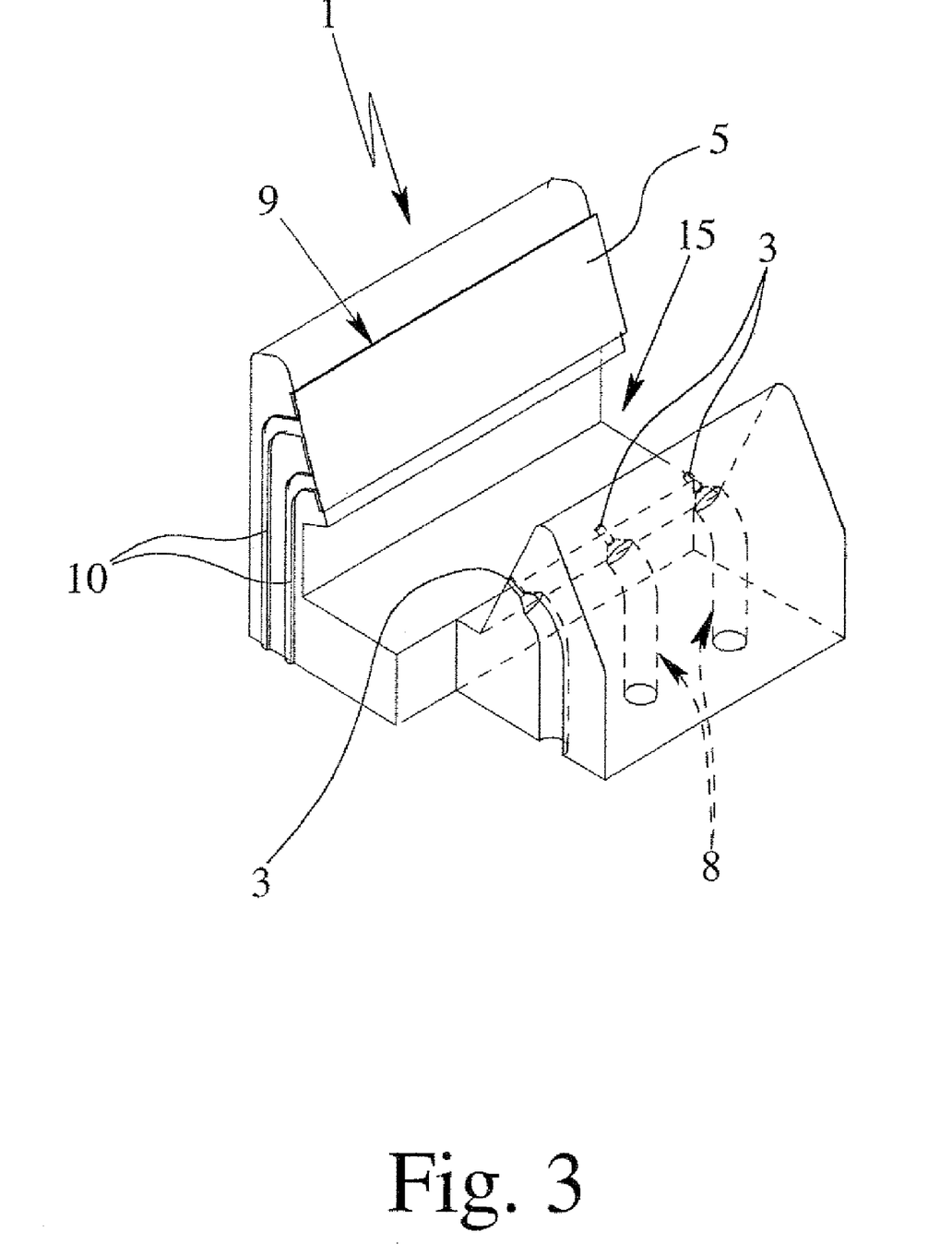
FIG. 3 is an enlarged view of the device according to FIG. 2.

FIG. 2 shows, in the form of a very schematic diagram, a second embodiment of the device 1 according to the present proposal. FIG. 3 shows the device 1 on an enlarged scale. In contrast to the first embodiment, the nozzle 3 and the contact surface 5 are, in this case, formed as a block or as one piece, in particular, as a mono-block. A compact, universally usable structural part is obtained which, due to the preferred very small distance between the contact surface 5 and the nozzle 3—as already discussed on the basis of the first embodiment—operates satisfactorily with very low liquid pressures of, in particular, less than 3 MPa.

In addition, the device 1 according to the second embodiment comprises a plurality of nozzles 3 that generate preferably at least substantially jets of the liquid 2 which, in particular, impact at different regions on the preferably common contact surface 5. The nozzles 3 are, in this embodiment, preferably provided with the liquid 2 via separate feed lines 8.

Furthermore, FIG. 3 shows a heating device 9 with electrical connections 10 that is associated with the contact surface 5. The heating device 9 is electrically operated and forms, possibly directly or with an appropriate coating, protective layer or the like, the contact surface 5.

Figure 4:
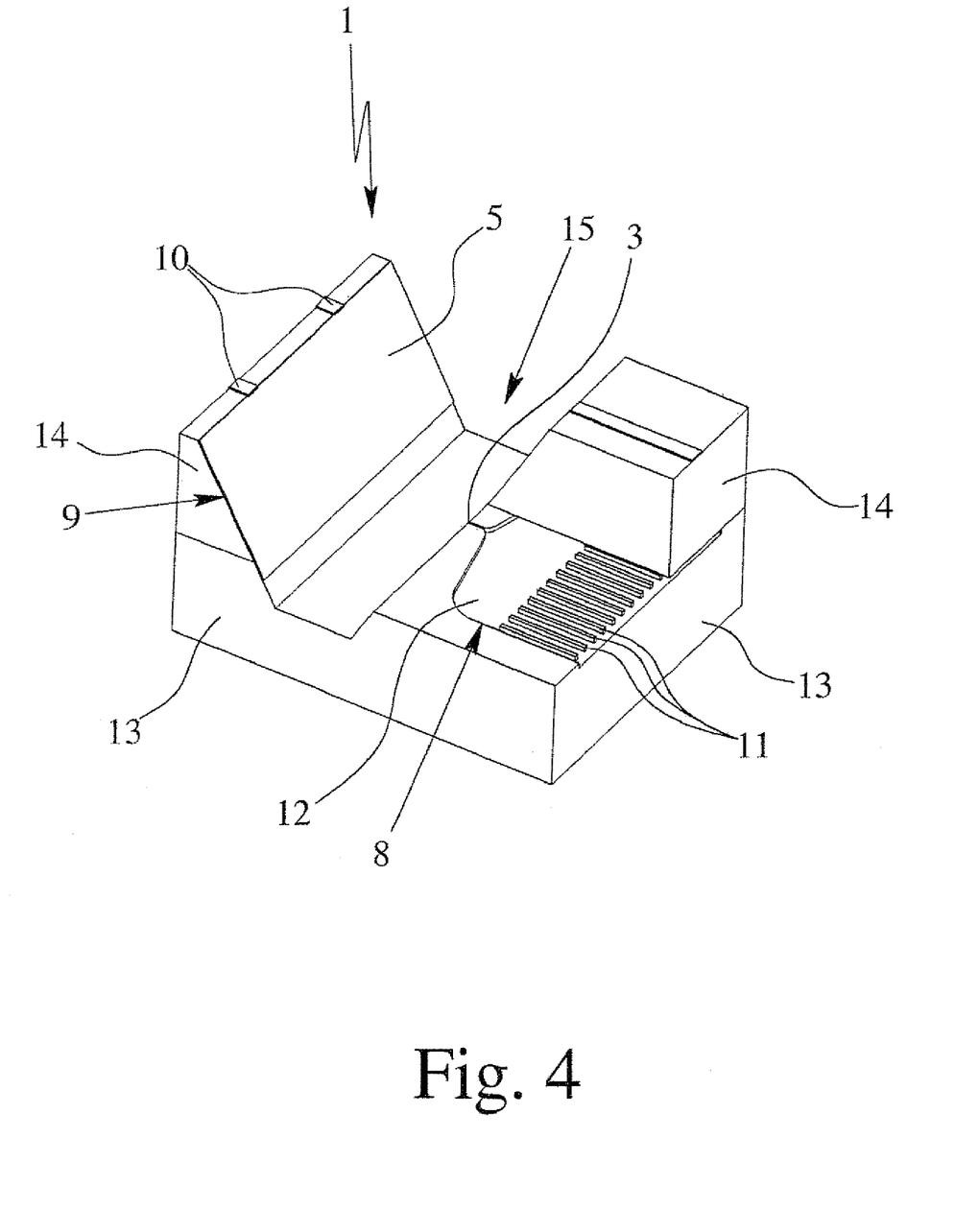
FIG. 4 is a diagrammatic view of a device in accordance with a third embodiment of the invention.

FIG. 4 shows in a perspective view a third embodiment of the device 1 according to the proposal with only one nozzle 3. The nozzle 3 and the contact and deflecting surface 5 are, in this case, also formed as a common—preferably multipart—structural part corresponding to the second embodiment.

The feed line 8 for the liquid 2 to the nozzle 3 has a plurality of parallel channels 11 that serve to filter the liquid 2 in order to prevent a blockage of the very fine nozzle 3. The channels 11 thus form a filter device. The channels 11 are connected in parallel to a subsidiary, common collecting region 12 that feeds the liquid 2 to the nozzle 3.

The channels 11, the collecting region 12 and/or the nozzle 3 are preferably formed by corresponding depressions in a surface of an, in particular, plate-shaped material piece 13, for example, by etching, laser abrasion, stamping, injection molding or the like, and are covered, in particular, by a cover 14, which has been partly cut away in FIG. 4 for the sake of clarity.

The nozzle 3, in the illustrated example, opens onto a side wall of a preferably groove-shaped recess 15. The oppositely-facing wall forms the contact and deflecting surface 5 and carries the heating device 9. In the illustrated example, the oppositely-facing wall is formed from the material piece 13 and the cover 14. However, other structural solutions are also possible in this case.

Figure 5:
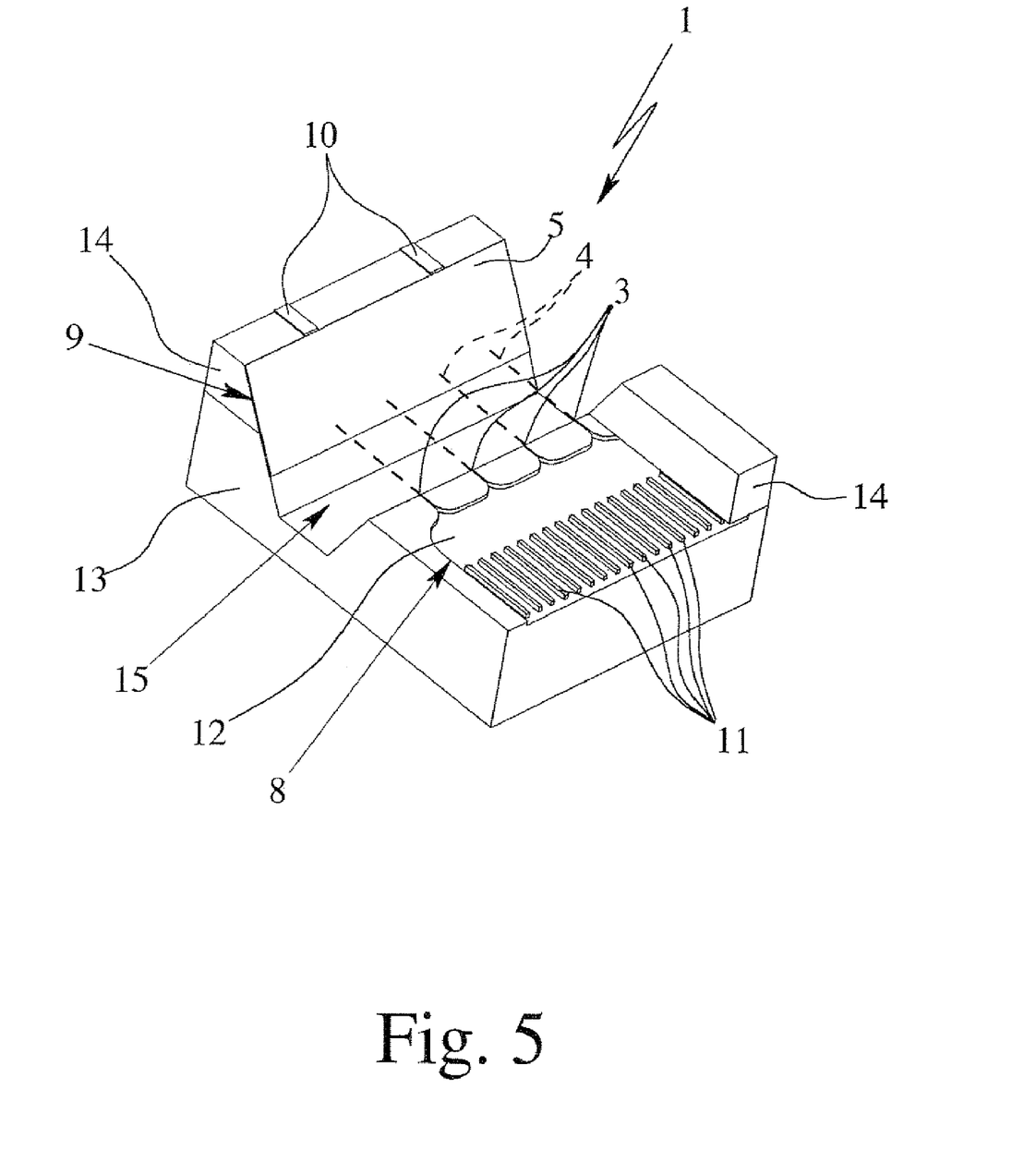
FIG. 5 is a diagrammatic view of a device in accordance with a fourth embodiment of the invention.

FIG. 5 is a diagrammatic, perspective representation of a fourth embodiment of the device 1 according to the invention. The fourth embodiment resembles the third embodiment, but instead of one nozzle 3, in this case, a plurality of nozzles 3 are provided, which are preferably connected in parallel to the common collecting region 12. Correspondingly, in the fourth embodiment, a plurality of jets 4 of the liquid 2 (shown only by dotted lines in FIG. 5) can be generated, which preferably strike different regions of the contact surface 5 and can be atomized in parallel in the desired manner to produce a common aerosol 7. This permits the atomization of a large amount of liquid 2 in a short time, in particular, at a rate of at least 30 µl/sec.

According to a variant (not illustrated), the jets 4 and individual groups of jets 4 strike different contact and deflecting surfaces 5. If necessary, the various surfaces 5 may then vary as regards their properties, in particular, distance to the respective nozzle 3, inclination, surface state, or the like.

The ejection of the liquid 2 to be atomized, in parallel and simultaneously through a plurality of nozzles 3, enables a large amount of liquid 2 to be atomized in a short time, whereby, as already explained, a relatively large amount of aerosol 7 with a small mean droplet size can be formed. This parallel and simultaneous ejection through a plurality of nozzles 3 may also be employed independently of the described embodiments and also independently of the proposed solution and atomization discussed here. Particularly preferably the parallel ejection through a plurality of nozzles 3 may also be employed in another type of atomizer, in particular the nebuliser obtainable under the trademark RESPIMAT®, or in an atomizer as disclosed in particular in International Patent Application Publications WO 91/14468 A1, WO 97/12687 A1 or WO 2005/080001 A1, wherein, for example, several pairs of jets of the liquid 2 to be atomized are generated by several nozzles 3 and the jets intersect in pairs for the atomization into small droplets.

The second, third and fourth embodiments of the device 1 according to the invention may be manufactured, in particular, on a miniaturized scale.

The device 1 according to the third and fourth embodiments is, in particular, produced by forming or recessing the nozzle(s) 3 and the feed line(s) 8 by etching in the material piece 13 on the side subsequently covered by the cover 14.

The material piece 13, preferably, are made of silicon. In particular, the piece is a silicon wafer or some other plate piece for a plurality of material pieces 13. The techniques known from semiconductor technology, such as lithography, covering with a photolacquer or the like, may therefore be used to form the structures.

The production of the structures, such as the nozzle 3, the feed line 8 and the like, preferably, takes place in the wafer or in another plate piece before the subdivision or the cutting up into the individual material pieces 13, i.e., in parallel and simultaneously for a plurality of devices 1.

The structured wafer or the other plate piece is then covered over the whole surface with the cover 14. The cover 14 preferably is made of glass or silicon, and is possibly also a silicon wafer or the like. The cover 14 is securely joined, preferably, by anodic bonding or another suitable method, to the wafer or plate piece forming the material pieces 13, to produce a plate composite.

The thickness of the lower layer and/or of the material piece 13 and/or of the cover 14 is, preferably, in each case, 200 to 800 μm, in particular, substantially about 500 μm.

Before forming the recess 15—possibly also before the connection to the material pieces 13—the cover 14 is preferably provided, on the flat side facing away from the material pieces 13, with a conducting structure for the subsequent formation of the electrical connections 10, in particular, by coating certain regions, partial removal of a corresponding, electrically conducting coating, or the like.

The recesses 15 of the devices 1 in the plate composite are then formed preferably in a thickness of about 100 to 300 μm, in particular, by suitably cutting into the plate composite with a suitable saw blade. The production of the recesses 15 may, however, be accomplished in another suitable way, for example, by laser abrasion, etching or the like. The nozzles 3 are formed and opened by the production of the recess(es) 15.

After the production of the recess(es) 15—and preferably, before the separation of the plate composite into individual devices 1—the heating devices 9 are formed in particular by vapor deposition of an electrically conducting material or by another coating method on the side wall(s) of the recess(es) 15 lying opposite the nozzle 3 and formation of a suitable conductor arrangement or guidance. An electrical connection to the connections 10 is produced at the same time. The exact structure of the heating devices 9 is not shown in FIGS. 4 & 5, since the heating devices 9 are preferably covered by a coating, protective layer or the like, not identified in more detail, formed in particular of silicon nitride, silicon carbide, Teflon or another suitable material, that forms the contact surface 5.

Finally, the plate composite is separated into the individual devices 1, in particular, by sawing or some other cutting or separation method.

The preferred sequence of steps explained hereinbefore permits a very simple and inexpensive production of the device 1 having defined properties and low tolerances.

The device 1 produced according to the proposal constitutes a common—optionally block-like and/or one-piece or integrated—structural part for the feed line(s) 8, the nozzle(s) 3, the contacts surface(s) 5 and possibly the heating device(s) 9. This arrangement allows a simple and rapid installation of the device 1, in particular, where the desired relationships of the nozzle 3 to the contact surface 5, especially a specific interspacing, have already been fixed by the device 1 according to the proposal.

FIG. 6 shows in a schematic, section-like view a device 1 in the form of an inhaler according to a fifth embodiment of the present invention.

The liquid 2 is stored in a container 16 and can be ejected through nozzle 3 as a jet 4 onto the heated contact surfaces 5 to partially vaporize the liquid 2 and form the aerosol 7 as explained above in connection with the other embodiments. The aerosol 7 is discharged via an optional mouthpiece 17.

The device 1/inhaler comprises, preferably, a supply means or pump 18. In the present case, the pump 18 comprises a supply tube 19, which is preferably connected with container 16 and extends into container 16 and into the liquid 2. The supply tube 19 extends with its other end into a pump chamber 20 and acts as a pump piston. A check valve 21 is preferably provided at the end of the supply tube 19 extending into the pump chamber 20.

The device 1 or pump 18 further comprises a preferably manually operated actuator 22. Preferably, the actuator 22 can be pivoted and acts with a curve 23 on a counter element 24 associated to the pump 18, container 16, and/or supply tube 19 directly or indirectly.

Figure 6:
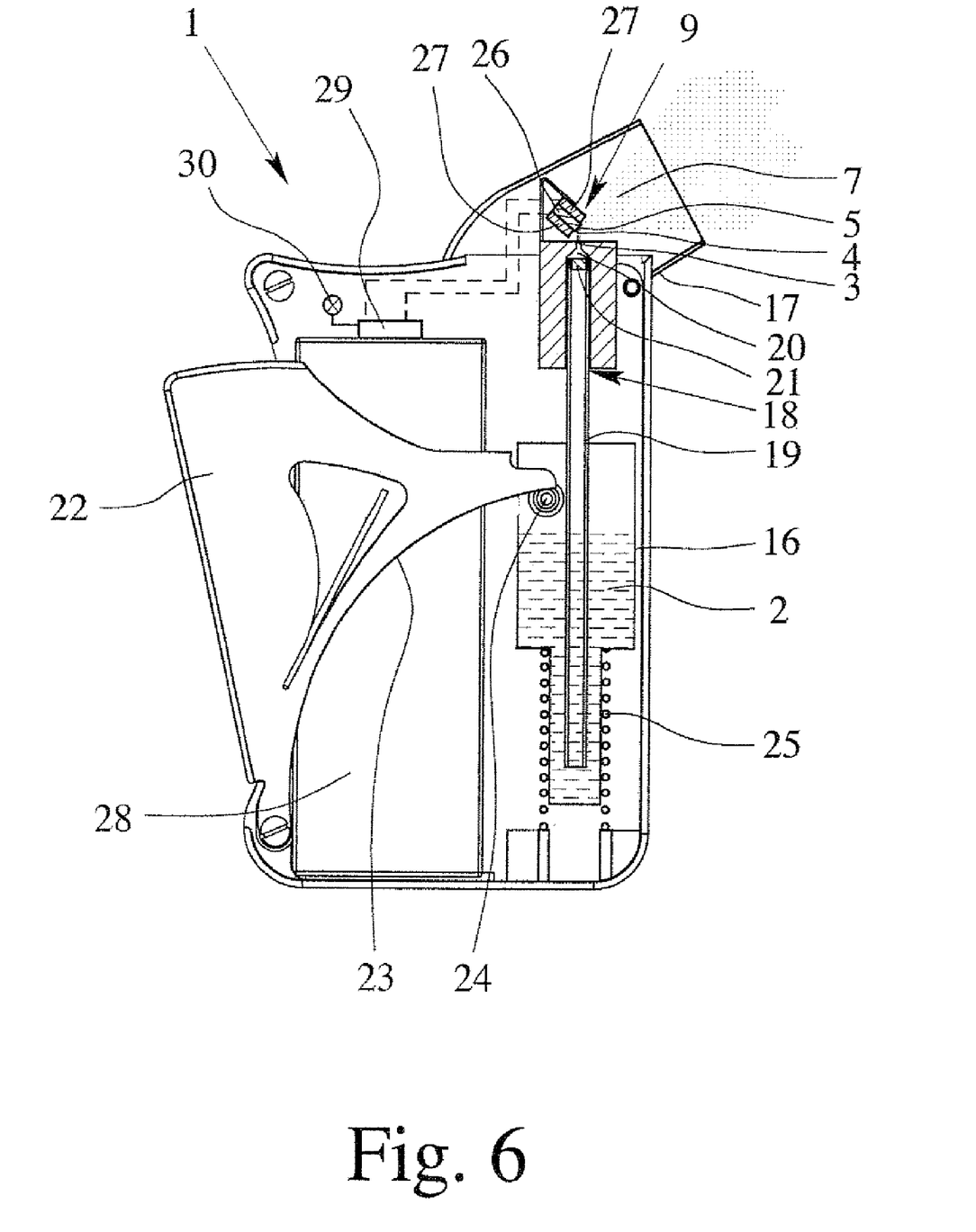
FIG. 6 is a diagrammatic cross-sectional view of a device in the form of an inhaler in accordance with a fifth embodiment of the invention.

When the actuator 22 is operated, in particular pressed or pivoted inwardly from the position shown in FIG. 6, the supply tube 19 and preferably the container 16 are moved downwardly from the position shown in FIG. 6. During this suction stroke, valve 21 is open and fluid 2 is drawn from the container 16 through the supply tube 19 into the pump chamber 20. Simultaneously, a spring 25 is biased that is directly or indirectly associated to the container 16 and/or supply tube 19.

At the end of the suction stroke, the biased spring 25 may be blocked in its biased or compressed position or may be released directly. If the spring 25 is blocked in its biased position, it may be released after release of the actuator 22 and/or after actuating any other release mechanism or the like.

With or after release, the force of the spring 25 is used to quickly return the supply tube 19—in FIG. 6 in upward direction—into the pump chamber 20, so that the valve 21 closes and a high fluid pressure is generated in the pump chamber 20 during the compression or pump stroke. Thus, the liquid 2 is ejected from the pump chamber 20 through nozzle 3 as jet 4 onto contact surface 5 as schematically shown in FIG. 6.

In the present embodiment, the contact surface 5 is formed preferably by an edge of a flat or plate-shaped a member 26. The member 26 is heated by at least one associated heating element 27 of the heating device 9, in particular sandwiched between two heating elements 27. The inhaler/heating device 9, preferably, comprises a battery or accumulator 28, in particular, a lithium ion accumulator or the like, for providing the necessary energy for powering the electrically operated heating elements 27.

Preferably, the heating device 9 additionally comprises a controller 29 and/or a display 30, e.g., a lamp or the like. Controller 29 controls the electric power supplied to the at least one heating elements 27 and may preferably control the temperature preferably of the member 26/contact surface 5.

The display 30 preferably indicates when the contact surface 5 has reached its temperature, the starting temperature T mentioned above, such as 250 to 400° C., so that the desired partial vaporization can take place when the jet 4 is directed onto the contact surface 5.

The heating device 9 may be switched on and/or off depending on the actuation of the pump 18. Vice versa, the pump 18 may be actuated and/or the spring 25 may be released from its biased position preferably only when the contact surface 5 has reached the desired/required temperature for generating the aerosol 7 in the desired manner as described above.

The battery/accumulator 28 may be exchanged and/or reloaded. For example, the device 1/inhaler may be inserted into and/or connected to—preferably wireless and/or inductively—to a charging device (not shown).

Preferably, the device 1/inhaler meters and dispenses the liquid 2 in defined doses (each pump stroke corresponds to one stroke), preferably, with about 10 to 100 μl as mentioned above. Preferably, the liquid is dispensed with a liquid flow of 5 to 100 μl/s, in particular, about 10 to 50 μl/s.

Alternatively or additionally, the above equation and/or other data and measures apply for the inhaler at least substantially.

The features of the different embodiments and the different embodiments can be combined any suitable manner and/or combined or used in other dispensers, inhalers or the like.

Preferably, the liquid 2 is, as already mentioned, a medicament formulation, for example an aqueous or ethanolic medicament formulation. It may however also involve another type of medicament formulation, a suspension or the like.

Preferred constituents and/or formulations of the preferably medicinal liquid 2 are listed hereinafter. As already mentioned, these may be aqueous or non-aqueous solutions, mixtures of ethanolic or solvent-free formulations or the like. Mixtures may contain in particular two or more, preferably three or four, medicaments, most preferably, in ethanolic formulations. The liquid 2 particularly preferably contains the following:

All inhalable compounds, for example, also inhalable macromolecules, as disclosed in European Patent EP 1 003 478, are used as pharmaceutically active substances. substance formulations or substance mixtures. Preferably, substances, substance formulations or substance mixtures that are used for inhalation purposes are employed to treat respiratory pathway conditions.

Particularly preferred in this context are medicaments that are selected from the group consisting of anticholinergic agents, betamimetics, steroids, phosphodiesterase IV inhibitors, LTD4 antagonists and EGFR kinase inhibitors, antiallergic agents, ergot alkaloid derivatives, triptanes, CGRP antagonists, phosphodiesterase V inhibitors, as well as combinations of such active substances, e.g. betamimetics plus anticholinergic agents or betamimetics plus antiallergic agents. In the case of combinations at least one of the active constituents contains preferably chemically bound water. Anticholinergic agent-containing active substances are preferably used, as single preparations or in the form of combination preparations.

The following, in particular, may be mentioned as examples of effective constituents or their salts:

Anticholinergics which may be used are preferably selected from among tiotropiumn bromide, oxitropium bromide, flutropium bromide, ipratropium bromide, glycopyrronium salts, trospium chloride, tolterodine, tropenol 2,2-diphenylpropionate methobromide, scopine 2,2-diphenylpropionate methobromide, scopine 2-fluoro-2,2-diphenylacetate methobromide, tropenol 2-fluoro-2,2-diphenylacetate methobromide, tropenol 3,3',4,4'-tetrafluorobenzilate methobromide, scopine 3,3',4,4'-tetrafluorobenzilate methobromide, tropenol 4,4'-difluorobenzilate methobromide, scopine 4,4'-difluorobenzilate methobromide, tropenol 3,3'-difluorobenzilate methobromide, scopine 3,3'-difluorobenzilate methobromide, tropenol 9-hydroxy-fluorene-9-carboxylate methobromide, tropenol 9-fluoro-fluorene-9-carboxylate methobromide, scopine 9-hydroxy-fluorene-9-carboxylate methobromide, scopine 9-fluoro-fluorene-9-carboxylate methobromide, tropenol 9-methyl-fluorene-9-carboxylate methobromide, scopine 9-methyl-fluorene-9-carboxylate methobromide, cyclopropyltropine benzilate methobromide, cyclopropyltropine 2,2-diphenylpropionate methobromide, cyclopropyltropine 9-hydroxy-xanthene-9-carboxylate methobromide, cyclopropyltropine 9-methyl-fluorene-9-carboxylate methobromide, cyclopropyltropine 9-methyl-xanthene-9-carboxylate methobromide, cyclopropyltropine 9-hydroxy-fluorene-9-carboxylate methobromide, cyclopropyltropine methyl 4,4'-difluorobenzilate methobromide, tropenol 9-hydroxy-xanthene-9-carboxylate methobromide, scopine 9-hydroxy-xanthene-9-carboxylate methobromide, tropenol 9-methyl-xanthene-9-carboxylate methobromide, scopine 9-methyl-xanthene-9-carboxylate methobromide, tropenol 9-ethyl-xanthene-9- carboxylate methobromide, tropenol 9-difluoromethyl-xanthene-9-carboxylate methobromide and scopine 9-hydroxymethyl-xanthene-9-carboxylate methobromide, optionally in the form of the racemates, enantiomers or diastereomers thereof and optionally in the form of the solvates and/or hydrates thereof.

Betamimetics which may be used are preferably selected from among albuterol, bambuterol, bitolterol, broxaterol, carbuterol, clenbuterol, fenoterol, formoterol, hexoprenaline, ibuterol, indacaterol, isoetharine, isoprenaline, levosalbutamol, mabuterol, meluadrine, metaproterenol, orciprenaline, pirbuterol, procaterol, reproterol, rimiterol, ritodrine, salmeterol, salmefamol, soterenot, sulphonterol, tiaramide, terbutaline, tolubuterol, CHF-1035, HOKU-81, KUL-1248, 3-(4-{6-[2-hydroxy-2-(4-hydroxy-3-hydroxymethyl-phenyl)-ethylamino]-hexyloxyl}-butyl)-benzolsulphonamide, 5-[2-(5,6-diethyl-indan-2-ylamino)-1-hydroxy-ethyl]-8-hydroxy-1H-quinolin-2-one, 4-hydroxy-7-[2-{[2-{[3-(2-phenylethoxy)propyl]sulphonyl}ethyl]-amino}ethyl]-2(3H)-benzothiazolone, 1-(fluoro-4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl) -2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluormethylphenyl)-2-tert.-butylamino) ethanol and 1-(4-ethoxycarbonylamino-3-cyano-5-fluorophenyl)-2-(tert.-butylamino)ethanol, optionally in the form of the racemates, enantiomers or diastereomers thereof and optionally in the form of the pharmaceutically acceptable acid addition salts, solvates and/or hydrates thereof Steroids which may be used are preferably selected from among prednisolone, prednisone, butixocortpropionate, RPR-106541, flunisolide, beclomethasone, triamcinolone, budesonide, fluticasone, mometasone, ciclesonide, rofleponide, ST-126, dexamethasone, (S)-fluoromethyl 6α, 9α-difluoro-17α-[(2-furanylcarbonyl)oxy]-11β-hydroxy-16α-methyl-3-oxo-androsta-1,4-diene-17β-carbothionate, (S)-(2-oxo-tetrahydro-furan-3S-yl) 6α,9α-difluoro-11β-hydroxy-16α-methyl-3-oxo-17α-propionyloxy-androsta-1,4-diene-17β-carbothionate and etiprednol-dichloroacetate (BNP-166), optionally in the form of the racemates, enantiomers or diastereomers thereof and optionally in the form of the salts and derivatives thereof, the solvates and/or hydrates thereof.

PDE IV-inhibitors which may be used are preferably selected from among enprofyllin, theophyllin, roflumilast, ariflo (cilomilast), CP-325,366, BY343, D-4396 (Sch-351591), AWD-12-281 (GW-842470), N-(3,5-dichloro-1-oxo-pyridin-4-yl)-4-difluoromethoxy-3-cyclopropyl-methoxybenzamide, NCS-613, pumafentine, (−)p-[(4αR*,10bS*)-9-ethoxy-1,2,3,4,4a,10b-hexahydro-8-methoxy-2-methylbenzo[s][1,6]naph-thyridin-6-yl]-N,N-diisopropyl-benzamnide, (R)-(+)-1-(4-bromobenzyl)-4-[(3-cyclo-pentyloxy)-4-methoxyphenyl]-2-pyrrolidone, 3-(cyclopentyloxy-4-methoxyphenyl)-1-(4-N'-[N-2-cyano-S-methyl-isothioureido]benzyl)-2-pyrrolidone, cis[4-cyano-4-(3-cyclopentyloxy-4-methoxyphenyl)cyclohexane-1-carboxylic acid], 2-carbomethoxy-4-cyano-4-(3-cyclopropylmethoxy-4-difluoromethoxyphenyl)cyclo-hexan-1-one, cis[4-cyano-4-(3-cyclopropylmethoxy-4-difluoromethoxyphenyl)cyclohexan-1-ol], (R)-(+)-ethyl[4-(3-cyclopentyloxy-4-methoxyphenyl)pyrrolidin-2-ylidene] acetate, (S)-(−)-ethyl[4-(3-cyclopentyloxy-4-methoxyphenyl)pyrrolidin-2-ylidene]acetate, CDP840, Bay-198004, D-4418, PD-168787, T-440, T-2585, arofyllin, atizoram, V-11294A, Cl-1018, CDC-801, CDC-3052, D-22888, YM-58997, Z-15370, 9-cyclopentyl-5,6-dihydro-7-ethyl-3-(2-thienyl)-9H-pyrazolo[3,4-c]-1,2,4-triazolo[4,3-a]pyridine and 9-cyclopentyl-5,6-dihydro-7-ethyl-3-(tert-butyl)-9H-pyrazolo[3,4-c]-1,2,4-triazolo[4,3-a]pyridin, optionally in the form of the racemates, enantiomers or diastereomers thereof and optionally in the form of the pharmacologically acceptable acid addition salts, solvates and/or hydrates thereof.

LTD4-antagonists which may be used are preferably selected from among montelukast, 1-(((R)-(3-(2-(6,7-difluoro-2-quinolinyl)ethenyl)phenyl)-3-(2-(2-hydroxy-2-propyl)phenyl)thio)methylcyclopropane-acetic acid, 1-(((1(R)-3(3-(2-(2,3-dichlorothieno[3,2-b]pyridin-5-yl)-(E)-ethenyl) phenyl)-3-(2-(1-hydroxy-1-methylethyl)-phenyl)propyl) thio)methyl)cyclopropane-acetic acid, pranlukast, zafirlukast, [2-[[2-(4-tert-butyl-2-thiazolyl)-5-benzofuranyl] oxymethyl]phenyl]acetic acid, MCC-847 (ZD-3523), MN-001, MEN-91507 (LM-1507), VUF-5078, VUF-K-8707 and L-733321, optionally in the form of the racemates, enantiomers or diastereomers thereof, optionally in the form of the pharmacologically acceptable acid addition salts thereof and optionally in the form of the salts and derivatives thereof, the solvates and/or hydrates thereof.

EGFR-kinase inhibitors which may be used are preferably selected from among cetuximab, trastuzumab, ABX-EGF, Mab ICR-62, 4-[(3-chloro-4-fluorophenyl)amino]-6-{[4-(morpholin-4-yl)-1-oxo-2-buten-1-yl]amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluoro-phenyl) amino]-6-{[4-((R)-6-methyl-2-oxo-morpholin-4-yl)-1-oxo-2-buten-1-yl]amino}7-[(S)-(tetrahydrofuran-3-yl)oxy]-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline, 4-[(3-chloro-4-fluorophenyl) amino]-6-{[4-(N,N-dimethylamino)-1-oxo-2-buten-1-yl] amino}-7-[(R)-(tetra-hydrofuran-2-yl)methoxy]-quinazoline, 4-[(3-ethynyl-phenyl)amino]-6,7-bis-(2-methoxy-ethoxy)-quinazoline, 4-[(R)-(1-phenyl-ethyl) amino]-6-(4-hydroxy-phenyl)-7H-pyrrolo[2,3-d] pyrimidine, 3-cyano-4-[(3-chloro-4-fluorophenyl)amino]-6-{[4-(N,N-dimethylamino)-1-oxo-2-buten-1-yl]amino}-7-ethoxy-quinoline, 4-[(R)-(1-phenyl-ethyl)amino]-6-{[4-((R)-6-methyl-2-oxo-morpholin-4-yl)-1-oxo-2-buten-1-yl] amino}-7-methoxy-quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline, 4-[(3-ethynyl-phenyl)amino]-6-{[4-(5,5-dimethyl-2-oxo-morpholin-4-yl)-1-oxo-2-buten-1-yl] amino}-quinazoline, 4-[(3-chloro-4-fluoro-phenyl)amino]-6-{2-[4-(2-oxo-morpholin-4-yl)-piperidin-1 -yl]-ethoxy}-7- methoxy-quinazoline, 4-[(3-chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-{1-[(morpholin-4-yl)carbonyl]-piperidin-4-yloxy}-7-methoxy-quinazoline, 4-[(3-chloro-4-fluoro-phenyl)amino]-6-(piperidin-3-yloxy)-7-methoxy-quinazoline, 4-[(3-chloro-4-fluoro-phenyl)amino]-6-[1-(2-acetylamino-ethyl)-piperidin-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-{trans-4-[(morpholin-4-yl)carbonylamino]-cyclohexan-1-yloxy}-7-methoxy-quinazoline, 4-[(3-chloro-4-fluoro-phenyl)amino]-6-{1-[piperidin-1-yl)carbonyl]-piperidin-4-yloxy}-7-methoxy-quinazoline, 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-(trans-4-ethansulphonylamino-cyclohexan-1-yloxy)-7-methoxy-quinazoline, 4-[(3-chloro-4-fluoro-phenyl)amino]-6-(1-methanesulphonyl-piperidin-4-yloxy)-7-(2-methoxy-ethoxy)-quinazoline, 4-[(3-chloro-4-fluoro-phenyl)amino]-6-[1-(2-methoxy-acetyl)-piperidin-4-yloxy]-7-(2-methoxy-ethoxy)-quinazoline, 4-[(3-ethynyl-phenyl)amino]-6-(tetrahydropyran-4-yloxy)-7-methoxy-quinazoline, 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline, 4-[(3-chloro-4-fluoro-phenyl)amino]-6-{cis-4-[(morpholin-4-yl)carbonylamino]-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-chloro-4-fluoro-phenyl)amino]-6-(1-methyl-piperidin-4-yloxy)-7(2-methoxy-ethoxy)-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(N-methyl-N-2-methoxyethyl-amino)carbonyl]-piperidin-4-yloxy}-7-methoxy-quinazoline, 4-[(3-chloro-4-fluoro-phenyl)amino]-6-(1-ethyl-piperidin-4-yloxy)-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluoro-phenyl)amino]-6-(1-methanesulphonyl-piperidin-4-yloxy)-7-methoxy-quinazoline, 4-[(3-chloro-4-fluoro-phenyl)amino]-6-(1-cyano-piperidin-4-yloxy)-7-methoxy-quinazoline, and 4-[(3-chloro-4-fluoro-phenyl)amino]-6-{1-[(2-methoxy-ethyl)carbonyl]-piperidin-4-yloxy}-7-methoxy-quinazoline, optionally in the form of the racemates, enantiomers or diastereomers thereof, optionally in the form of the pharmacologically acceptable acid addition salts thereof the solvates and/or hydrates thereof.

By acid addition salts, salts with pharmacologically acceptable acids which the compounds may possibly be capable of forming are meant, for example, salts selected from among the hydrochloride, hydrobromide, hydriodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

Examples of antiallergics are: disodium cromoglycate, nedocromil.

Examples of derivatives of the ergot alkaloids are: dihydroergotamine, ergotamine.

For inhalation, it is possible to use medicaments, pharmaceutical formulations and mixtures including the abovementioned active constituents, as well as their salts, esters and combinations of these active constituents, salts and esters.

What is claimed is:

1. Method for the atomization of a liquid, comprising the steps of:
   directing a liquid as a jet onto a hot or heated contact surface and,
   partially vaporizing the liquid with hot or heated contact surface in order to atomize the liquid in a non-directed manner into small droplets and generating an aerosol.

2. Method according to claim 1, wherein small amounts of the liquid are atomized in at least one of in succession and in parallel.

3. Method according to claim 2, wherein each individual amount is atomized into a plurality of droplets.

4. Method according to claim 1, wherein the liquid (2) is atomized into droplets without employing side walls.

5. Method according to claim 1, wherein the volume flow of the atomized liquid is at least 30 μl/sec.

6. Method according to claim 1, wherein the liquid (2) is delivered during the atomization at least one of continuously, only in the form of a defined or focused jet and as a free jet (4) onto the contact surface (5).

7. Method according to claim 1, wherein the jet diameter is adjusted, controlled or regulated in order to achieve at least one of a desired droplet size, propagation velocity of the aerosol and a jet diameter is less than 1 to 50 μm.

8. Method according to claim 1, wherein the aerosol (7) is metered by metering the jet (4).

9. Method according to claim 1, wherein the liquid flow or jet flow is dispensed at at least one of about 5 to 100 μl/s in metered doses of about 10 to 100 μl.

10. Method according to claim 6, wherein the liquid is dispensed as a free jet having a length that is less that 1 mm.

11. Method according to claim 1, wherein the liquid (2) is delivered for the atomization simultaneously in a plurality of jets (4).

12. Method according to claim 1, wherein the liquid (2) is deflected on the contact surface.

13. Method according to claim 1, wherein the temperature of the contact surface (5) is adjusted, controlled or regulated in order to achieve at least one of a desired droplet size and propagation velocity of the aerosol (7).

14. Method according to claim 1, wherein the temperature of the contact surface (5) is at least 20° C. above at least of a constituent of the liquid.

15. Method according to claim 1, wherein the contact surface (5) is at least one of electrically heated, heated by light radiation and chemically heated.

16. Method according to claim 1, wherein the liquid (2) impacts at an angle of 10° to 90° on the contact surface (5).

17. Method according to claim 1, wherein the impact angle of the liquid (2) on the contact surface (5) is adjusted, controlled or regulated in order to achieve at least one of a desired droplet size and propagation velocity of the aerosol (7).

18. Method according to claim 1, wherein the liquid (2) is delivered at, or strikes the contact surface (5) at a pressure of 0.05 to 3 MPa.

19. Method according to claim 1, wherein the delivery pressure of the liquid (2) is adjusted, controlled or regulated in order to achieve at least one of a desired droplet size and propagation velocity of the aerosol (7).

20. Method according to claim 1, wherein the aerosol (7) is generated only by at least one of partial vaporization and the liquid being directed only as a focused or defined jet (4) of liquid (2) onto the contact surface (5).

21. Method according to claim 1, wherein only up to 15 Vol. % of the liquid (2) is vaporized when impinging onto the contact surface (5).

22. Method according to claim 1, wherein the propagation velocity of the aerosol (7) is less than 1 m/sec.

23. Method according to claim 1, wherein at least one of the mean diameter of the droplets (6) is less than 10 μm and the mean volume of the droplets (6) is less than 1 pl.

24. Method according to claim 1, wherein a medicament formulation or a cosmetic agent is used as liquid (2) and atomized.

* * * * *